(12) United States Patent
Herbowy et al.

(10) Patent No.: US 8,182,525 B2
(45) Date of Patent: *May 22, 2012

(54) METHODS AND SYSTEMS FOR ENDOVASCULAR ANEURYSM TREATMENT

(75) Inventors: Steven L. Herbowy, Palo Alto, CA (US); Matthew R. Hellewell, Lehi, UT (US); K. T. Venkateswara Rao, San Jose, CA (US); Michael A. Evans, Palo Alto, CA (US); Thomas Howell, Palo Alto, CA (US); Gwendolyn A. Watanabe, Sunnyvale, CA (US); Bhupendra Shah, San Ramon, CA (US); James McKinley, Woodside, CA (US)

(73) Assignee: Endologix, Inc., Irvine, CA (US)

( * ) Notice: Subject to any disclaimer, the term of this patent is extended or adjusted under 35 U.S.C. 154(b) by 276 days.

This patent is subject to a terminal disclaimer.

(21) Appl. No.: 12/421,297

(22) Filed: Apr. 9, 2009

(65) Prior Publication Data

US 2009/0198267 A1   Aug. 6, 2009

Related U.S. Application Data

(63) Continuation of application No. 11/187,471, filed on Jul. 22, 2005, now Pat. No. 7,530,988.

(60) Provisional application No. 60/589,850, filed on Jul. 22, 2004.

(51) Int. Cl.
*A61F 2/06* (2006.01)
(52) U.S. Cl. .............. 623/1.25; 606/195; 623/1.32
(58) Field of Classification Search .......... 606/191, 606/192, 194, 195, 200; 623/1.25, 1.27, 623/1.32
See application file for complete search history.

(56) References Cited

U.S. PATENT DOCUMENTS

| | | | |
|---|---|---|---|
| 4,641,653 A | | 2/1987 | Rockey |
| 4,728,328 A | | 3/1988 | Hughes et al. |
| 5,222,970 A | * | 6/1993 | Reeves .................. 606/195 |
| 5,330,528 A | | 7/1994 | Lazim |
| 5,530,528 A | | 6/1996 | Houki et al. |
| 5,534,024 A | | 7/1996 | Rogers et al. |
| 5,665,117 A | * | 9/1997 | Rhodes .................. 623/1.1 |
| 5,693,088 A | | 12/1997 | Lazarus |
| 5,769,882 A | | 6/1998 | Fogarty et al. |
| 5,785,679 A | | 7/1998 | Abolfathi et al. |

(Continued)

FOREIGN PATENT DOCUMENTS

FR   2834199 A1   4/2003

(Continued)

OTHER PUBLICATIONS

Gilling-Smith, "Stent Graft Migration After Endovascular Aneurysm Repair," presented at 25th International Charing Cross Symposium, Apr. 13, 2003 [Power Point Presentation and Transcript], 56 pages total.

(Continued)

*Primary Examiner* — Darwin Erezo
(74) *Attorney, Agent, or Firm* — Kilpatrick Townsend & Stockton LLP

(57) ABSTRACT

Aneurysms are treated by filling a double-walled filling structure with a curable medium. The structures may be delivered over balloon deployment mechanisms in order to shape and open tubular lumens therethrough. The filling structures are preferably used in pairs for providing flow into the iliac arteries when treating abdominal aortic aneurysm.

21 Claims, 14 Drawing Sheets

U.S. PATENT DOCUMENTS

| | | | |
|---|---|---|---|
| 5,824,037 A | 10/1998 | Fogarty et al. | |
| 5,843,160 A | 12/1998 | Rhodes | |
| 5,846,261 A | 12/1998 | Kotula et al. | |
| 5,876,448 A | 3/1999 | Thompson et al. | |
| 5,931,866 A | 8/1999 | Frantzen | |
| 5,994,750 A | 11/1999 | Yagi | |
| 6,022,359 A | 2/2000 | Frantzen | |
| 6,083,259 A | 7/2000 | Frantzen | |
| 6,110,198 A | 8/2000 | Fogarty et al. | |
| 6,123,715 A | 9/2000 | Amplatz | |
| 6,168,592 B1 | 1/2001 | Kupiecki et al. | |
| 6,187,034 B1 | 2/2001 | Frantzen | |
| 6,190,402 B1 | 2/2001 | Horton et al. | |
| 6,193,745 B1 | 2/2001 | Fogarty et al. | |
| 6,196,230 B1 | 3/2001 | Hall et al. | |
| 6,231,562 B1 | 5/2001 | Khosravi et al. | |
| 6,235,050 B1 | 5/2001 | Quiachon et al. | |
| 6,261,305 B1 | 7/2001 | Marotta et al. | |
| 6,283,991 B1 | 9/2001 | Cox et al. | |
| 6,296,603 B1 | 10/2001 | Turnlund et al. | |
| 6,299,597 B1 | 10/2001 | Buscemi et al. | |
| 6,312,462 B1 | 11/2001 | McDermott et al. | |
| 6,312,463 B1 | 11/2001 | Rourke et al. | |
| 6,331,184 B1 | 12/2001 | Abrams | |
| 6,334,869 B1 | 1/2002 | Leonhardt et al. | |
| 6,375,675 B2 | 4/2002 | Dehdashtian et al. | |
| 6,409,757 B1 | 6/2002 | Trout, III et al. | |
| 6,463,317 B1 * | 10/2002 | Kucharczyk et al. | 600/411 |
| 6,506,204 B2 | 1/2003 | Mazzocchi | |
| 6,544,276 B1 | 4/2003 | Azizi | |
| 6,576,007 B2 | 6/2003 | Dehdashtian et al. | |
| 6,592,614 B2 | 7/2003 | Lenker et al. | |
| 6,613,037 B2 | 9/2003 | Khosravi et al. | |
| 6,656,214 B1 | 12/2003 | Fogarty et al. | |
| 6,663,607 B2 | 12/2003 | Slaikeu et al. | |
| 6,663,667 B2 | 12/2003 | Dehdashtian et al. | |
| 6,692,486 B2 | 2/2004 | Jaafar et al. | |
| 6,695,833 B1 | 2/2004 | Frantzen | |
| 6,730,119 B1 | 5/2004 | Smalling | |
| 6,773,454 B2 | 8/2004 | Wholey et al. | |
| 6,827,735 B2 | 12/2004 | Greenberg | |
| 6,843,803 B2 | 1/2005 | Ryan et al. | |
| 6,918,926 B2 | 7/2005 | Letort | |
| 6,960,227 B2 | 11/2005 | Jones et al. | |
| 7,131,991 B2 | 11/2006 | Zarins et al. | |
| 7,147,661 B2 | 12/2006 | Chobotov et al. | |
| 7,530,988 B2 * | 5/2009 | Evans et al. | 606/195 |
| 7,666,220 B2 * | 2/2010 | Evans et al. | 623/1.25 |
| 7,682,383 B2 * | 3/2010 | Robin | 623/1.21 |
| 2002/0026217 A1 | 2/2002 | Baker et al. | |
| 2003/0014075 A1 | 1/2003 | Rosenbluth et al. | |
| 2003/0051735 A1 | 3/2003 | Pavcnik et al. | |
| 2003/0130725 A1 | 7/2003 | DePalma et al. | |
| 2003/0135269 A1 | 7/2003 | Swanstrom | |
| 2003/0204249 A1 | 10/2003 | Letort | |
| 2003/0216802 A1 | 11/2003 | Chobotov | |
| 2004/0016997 A1 | 1/2004 | Ushio | |
| 2004/0044358 A1 | 3/2004 | Khosravi et al. | |
| 2004/0082989 A1 | 4/2004 | Cook et al. | |
| 2004/0098096 A1 | 5/2004 | Eton | |
| 2004/0167607 A1 | 8/2004 | Frantzen | |
| 2004/0204755 A1 * | 10/2004 | Robin | 623/1.21 |
| 2005/0004660 A1 | 1/2005 | Rosenbluth et al. | |
| 2005/0028484 A1 | 2/2005 | Littlewood | |
| 2005/0065592 A1 | 3/2005 | Holzer | |
| 2006/0025853 A1 | 2/2006 | Evans et al. | |
| 2006/0212112 A1 | 9/2006 | Evans et al. | |
| 2007/0150041 A1 | 6/2007 | Evans et al. | |
| 2007/0276477 A1 | 11/2007 | Lee et al. | |
| 2008/0039923 A1 | 2/2008 | Taylor et al. | |
| 2009/0198267 A1 | 8/2009 | Evans et al. | |
| 2009/0318949 A1 | 12/2009 | Ganpath et al. | |
| 2009/0319029 A1 | 12/2009 | Evans et al. | |
| 2010/0004728 A1 | 1/2010 | Rao et al. | |
| 2010/0036360 A1 | 2/2010 | Herbowy et al. | |

FOREIGN PATENT DOCUMENTS

| | | |
|---|---|---|
| WO | WO 00/51522 | 9/2000 |
| WO | WO 01/21108 | 3/2001 |
| WO | WO 01/66038 | 9/2001 |
| WO | WO 02/102282 | 12/2002 |
| WO | WO 03/037222 A2 | 5/2003 |
| WO | WO 2004/045393 A2 | 6/2004 |

OTHER PUBLICATIONS

Carmi et al., "Endovascular stent-graft adapted to the endoluminal environment: prototype of a new endoluminal approach," J Endovasc Ther. Jun. 2002;9(3):380-381.

Supplementary European Search Report and Search Opinion of EP Patent Application No. 05773726, mailed Apr. 23, 2010, 6 pages total.

* cited by examiner

METHODS AND SYSTEMS FOR ENDOVASCULAR ANEURYSM TREATMENT

CROSS-REFERENCES TO RELATED APPLICATIONS

This application is a continuation of U.S. patent application Ser. No. 11/187,471, filed on Jul. 22, 2005, now issued as U.S. Pat. No. 7,530,988 on May 12, 2009, which claims the benefit of prior Provisional Application No. 60/589,850, filed on Jul. 22, 2004, the full disclosures of which are incorporated herein by reference.

BACKGROUND OF THE INVENTION

1. Field of the Invention

The present invention relates generally to medical apparatus and methods for treatment. More particularly, the present invention relates to expandable prosthesis and methods for treating abdominal and other aneurysms.

Aneurysms are enlargements or "bulges" in blood vessels which are often prone to rupture and which therefore present a serious risk to the patient. Aneurysms may occur in any blood vessel but are of particular concern when they occur in the cerebral vasculature or the patient's aorta.

The present invention is particularly concerned with aneurysms occurring in the aorta, particularly those referred to as aortic aneurysms. Abdominal aortic aneurysms (AAA's) are classified based on their location within the aorta as well as their shape and complexity. Aneurysms which are found below the renal arteries are referred to as infrarenal abdominal aortic aneurysms. Suprarenal abdominal aortic aneurysms occur above the renal arteries, while thoracic aortic aneurysms (TAA's) occur in the ascending, transverse, or descending part of the upper aorta.

Infrarenal aneurysms are the most common, representing about seventy percent (70%) of all aortic aneurysms. Suprarenal aneurysms are less common, representing about 20% of the aortic aneurysms. Thoracic aortic aneurysms are the least common and often the most difficult to treat. Most or all present endovascular systems are also too large (above 12 F) for percutaneous introduction.

The most common form of aneurysm is "fusiform," where the enlargement extends about the entire aortic circumference. Less commonly, the aneurysms may be characterized by a bulge on one side of the blood vessel attached at a narrow neck. Thoracic aortic aneurysms are often dissecting aneurysms caused by hemorrhagic separation in the aortic wall, usually within the medial layer. The most common treatment for each of these types and forms of aneurysm is open surgical repair. Open surgical repair is quite successful in patients who are otherwise reasonably healthy and free from significant co-morbidities. Such open surgical procedures are problematic, however, since access to the abdominal and thoracic aortas is difficult to obtain and because the aorta must be clamped off, placing significant strain on the patient's heart.

Over the past decade, endoluminal grafts have come into widespread use for the treatment of aortic aneurysm in patients who cannot undergo open surgical procedures. In general, endoluminal repairs access the aneurysm "endoluminally" through either or both iliac arteries in the groin. The grafts, which typically have been fabric or membrane tubes supported and attached by various stent structures are then implanted, typically requiring several pieces or modules to be assembled in situ. Successful endoluminal procedures have a much shorter recovery period than open surgical procedures.

Present endoluminal aortic aneurysm repairs, however, suffer from a number of limitations. A significant number of endoluminal repair patients experience leakage at the proximal juncture (attachment point closest to the heart) within two years of the initial repair procedure. While such leaks can often be fixed by further endoluminal procedures, the need to have such follow-up treatments significantly increases cost and is certainly undesirable for the patient. A less common but more serious problem has been graft migration. In instances where the graft migrates or slips from its intended position, open surgical repair is required. This is a particular problem since the patients receiving the endoluminal grafts are those who are not considered good candidates for open surgery. Further shortcomings of the present endoluminal graft systems relate to both deployment and configuration. The multiple component systems require additional time for introducing each piece and even more time for assembling the pieces in situ. Such techniques are not only more time consuming, they are also more technically challenging, increasing the risk of failure. Current devices are also unsuitable for treating many geometrically complex aneurysms, particularly infrarenal aneurysms with little space between the renal arteries and the upper end of the aneurysm, referred to as short-neck or no-neck aneurysms. Aneurysms having torturous geometries, are also difficult to treat.

For these reasons, it would desirable to provide improved methods, systems, and prosthesis for the endoluminal treatment of aortic aneurysms. Such improved methods, systems, and treatments should preferably provide implanted prosthesis which result in minimal or no endoleaks, which resist migration, which are relatively easy to deploy, which have a low introduction profile (preferably below 12 F), and which can treat most or all aneurismal configurations, including short-neck and no-neck aneurysms as well as those with highly irregular and asymmetric geometries. At least some of these objectives will be met by the inventions described hereinafter.

2. Description of the Background Art

Grafts and endografts having fillable components are described in U.S. Pat. Nos. 4,641,653; 5,530,528; 5,665,117; and 5,769,882; U.S. Patent Publications 2004/0016997; and PCT Publications WO 00/51522 and WO 01/66038.

BRIEF SUMMARY OF THE INVENTION

The present invention provides methods, systems, and prosthesis for the endoluminal treatment of aneurysms, particularly aortic aneurysms including both abdominal aortic aneurysms (AAA's) and thoracic aortic aneurysms (TAA's). The prosthesis comprise double-walled filling structures which are pre-shaped and otherwise adapted to substantially fill the enlarged volume of an aneurysm, particularly a fusiform aneurysm, leaving a lumen in place for blood flow.

The double-walled filling structures will thus usually have a generally toroidal structure with an outer wall, an inner wall, a potential space or volume between the outer and inner walls to be filled with a filling medium, and a generally tubular lumen inside of the inner wall which provides the blood flow lumen after the prosthesis has been deployed. The shape of the filling structure will be preferably adapted to conform to the aneurysm being treated. In some instances, the filling structure can be shaped for the aneurismal geometry of a particular patient using imaging and computer-aided design and fabrication techniques. In other instances, a family or collection of filling structures will be developed having different geometries and sizes so that a treating physician may select a specific filling structure to treat a particular patient based on the size and geometry of that patient's aneurysm. In all instances, the outer wall of the filling structure will conform or be conformable to the inner surface of the aneurysm being treated. While the inner wall of the structure will be aligned with lumens of the blood vessels on either side of the prosthesis after the prosthesis has been deployed.

The filling structures of the prosthesis will usually be formed from a non-compliant material, such as parylene, Dacron, PET, PTFE, a compliant material, such as silicone, polyurethane, latex, or combinations thereof. Usually, it will be preferred to form at least the outer wall partially or entirely from a non-compliant material to enhance conformance of the outer wall to the inner surface of the aneurysm. This is particularly true when the aneurysm has been individually designed and/or sized for the patient being treated.

The walls of the filling structures may consist of a single layer or may comprise multiple layers which are laminated or otherwise formed together. Different layers may comprise different materials, including both compliant and/or non-compliant materials. The structure walls may also be reinforced in various ways, including braid reinforcement layers, filament reinforcement layers, and the like. In some instances, it would be possible to include self-expanding scaffolds within the filling structures so that the structures could be initially delivered and be allowed to self-expand at the treatment site, thus obviating the need for an expansion delivery catheter as described as the preferred embodiment below.

Preferred delivery protocols will utilize delivery catheters having a balloon or other expandable support for carrying the filling structure. When using balloons, the balloons will preferably be substantially or entirely compliant, although non-compliant and combination compliant/non-compliant balloons may also find use. The balloon or other mechanical expansion components of the delivery catheter will initially be disposed within the inner tubular lumen of the filling structure, with the filling structure generally being collapsed into a low width or low profile configuration over the expansion element. The delivery catheter may then be introduced intraluminally, typically into the iliac artery and upwardly to the region within the aorta to be treated. The delivery catheter will also include one or more lumens, tubes, or other components or structures for delivering the filling medium in a fluid form to an internal filling cavity of the filling structure. Thus, the delivery catheter can be used to both initially place and locate the filling structure of the prosthesis at the aneurismal site. Once at the aneurismal site, the internal tubular lumen of the structure can be expanded using the balloon or other expandable element on the delivery catheter. The filling structure itself will be filled and expanded by delivering the filling medium via the catheter into the internal volume of the filling structure. Both expansion and filling operations may be performed simultaneously, or can be performed in either order, i.e. the filling structure may be filled first with the delivery catheter balloon being expanded second, or vice versa. The filling structure(s) and/or delivery balloons may have radiopaque markers to facilitate placement and/or pressure sensors for monitoring filling and inflation pressures during deployment.

In preferred aspects of the present invention, the filling structure will be filled with a fluid (prior to hardening as described herein below) at a pressure which is lower than that of the expansion force provided by the delivery catheter, typically the filling pressure of the expandable balloon. Typically, the filling structure will be filled with filling medium at a pressure from 80 mm of Hg to 1000 mm of Hg, preferably from 200 mm of Hg to 600 mm of Hg, while the delivery balloon is inflated to a pressure in the range from 100 mm of Hg to 5000 mm of Hg, preferably from 400 mm of Hg to 1000 mm of Hg. These pressures are gage pressures, i.e. measured relative to atmospheric pressure.

As described thus far, in the present invention includes delivery of a single prosthesis and filling structure to an aneurysm. Delivery of a single filling structure will be particularly suitable for aneurysms which are remote from a vessel bifurcation so that both ends of the filling structure are in communication with only a single blood vessel lumen. In the case of aneurysms located adjacent a vessel bifurcation, such as the most common infrarenal abdominal aortic aneurysms, it will often be preferable to utilize two such filling structures introduced in a generally adjacent, parallel fashion within the aneurismal volume. In the specific case of the infrarenal aneurysms, each prosthesis will usually be delivered separately, one through each of the two iliac arteries. After locating the filling structures of the prosthesis within the aneurismal space, they can be filled simultaneously or sequentially to fill and occupy the entire aneurismal volume, leaving a pair of blood flow lumens.

Suitable filling materials will be fluid initially to permit delivery through the delivery catheter and will be curable or otherwise hardenable so that, once in place, the filling structure can be given a final shape which will remain after the delivery catheter is removed. The fillable materials will usually be curable polymers which, after curing, will have a fixed shape with a shore hardness typically in the range from 10 durometer to 140 durometer. The polymers may be delivered as liquids, gels, foams, slurries, or the like. In some instances, the polymers may be epoxies or other curable two-part systems. In other instances, the polymer may comprise a single material which when exposed to the vascular environment within the filling structure changes state over time, typically from zero to ten minutes.

In a preferred aspect of the present invention, after curing, the filling material will have a specific gravity, typically in the range from 0.1 to 5, more typically from 0.8 to 1.2 which is generally the same as blood or thrombus. The filling material may also include bulking and other agents to modify density, viscosity, mechanical characteristics or the like, including microspheres, fibers, powders, gasses, radiopaque materials, drugs, and the like. Exemplary filling materials include polyurethanes, collagen, polyethylene glycols, microspheres, and the like.

Preferably, the filling structures of the prosthesis will require no additional sealing or anchoring means for holding them in place within the aneurysm. In some instances, however, it may be desirable to employ such additional sealing or anchoring mechanisms, such as stents, scaffolds, hooks, barbs, sealing cuffs, and the like. For sealing cuffs or stents which extend proximately of infrarenal prosthesis, it may be desirable to provide openings or ports to allow the anchoring or sealing devices to extend over the renal ostia while penetrating blood flow into the renal arteries. The sealing or anchoring devices will typically be attached to and/or overlap with the filling structure of the prosthesis and will provide for a smooth transition from the aortic and/or iliac lumens into the tubular lumens provided by the deployed filling structures.

The filling structures may be modified in a variety of other ways within the scope of the present invention. For example, the external surfaces of the filling structures may be partially or entirely modified to enhance placement within the aneurismal space, typically by promoting tissue ingrowth or mechanically interlocking with the inner surface of the aneurysm. Such surface modifications include surface roughening, surface stippling, surface flocking, fibers disposed over the surface, foam layers disposed over the surface, rings, and the like. It is also possible to provide biologically active substances over all or a portion of the external surface of the filling structure, such as thrombogenic substances, tissue growth promotants, biological adhesives, and the like. It would further be possible to provide synthetic adhesives, such as polyacrylamides, over the surface to enhance adherence.

In some instances, it will be desirable to modify all or a portion of the internal surface of the filling cavity of the filling structure. Such surface modifications may comprise surface roughening, rings, stipples, flocking, foam layers, fibers, adhesives, and the like. The purpose of such surface modification will usually be to enhance the filling and bonding to the filling material, and to control the minimum wall thickness when the structure is filled particularly after the filling material has been cured. In particular instances, in locations of the filling structure which will be pressed together when the structure is deployed, thus potentially excluding filling material, it will be desirable if the surfaces of the filling structure can adhere directly to each other.

In view of the above general descriptions of the present invention, the following specific embodiments may be better understood. In a first specific embodiment, methods for treating an aneurysm comprise positioning at least one double-walled filling structure across the aneurysm. By "across" the aneurysms, it is meant generally that the filling structure will extend axially from one anatomical location which has been identified by imaging or otherwise as the beginning of the aneurysm to a space-part location (or locations in the case of bifurcated aneurysm) where it has been established that the aneurysm ends. After positioning, the at least one filling structure is filled with a fluid filling medium so that an out wall of the structure conforms to the inside of the aneurysm and an inner wall of the structure forms a generally tubular lumen to provide for blood flow after the filling structure has been deployed. The tubular lumen will preferably be supported, typically by a balloon or mechanically expansible element, while the filling structure is being filled, after the filling structure has been filled, or during both periods. After the filling structure has been filled, the filling material or medium is hardened while the tubular lumen remains supported. Supporting the tubular lumen during hardening assures that the lumen will have a desired geometry, will properly align with adjacent vascular lumens and that the tubular lumen being formed remains aligned with the native aortic and/or iliac artery lumens after the prosthesis has been fully implanted. Preferably, the support will be provided by a balloon which extends proximally and distally of the filling structure where the balloon may slightly "overexpand" in order to assure the desired smooth transition and conformance of the tubular lumen provided by the filling structure with the native vessel lumens.

After hardening, the support will be removed, leaving the filling structure in place. In some instances, however, prior to hardening, it will be desirable to confirm proper placement of the filling structure. This can be done using imaging techniques or otherwise testing for patency and continuity. In some instances, it may be desirable to first fill the filling structure with saline or other non-hardenable substance to make sure that the geometry of the filling structure is appropriate for the patient being treated. After testing, the saline may be removed and replaced with the hardenable filler.

In a second specific embodiment of the present invention, abdominal aortic aneurysms and other bifurcated aneurysms are treated by positioning first and second double-walled filling structures within the aneurismal volume. The first and second double-walled filling structures are positioned across the aneurysm, as defined above, extending from the aorta beneath the renal arteries to each of the iliac arteries, respectively. The first fluid filling structure is filled with a fluid filling material, the second filling structure is also filled with a fluid material, and the outer walls of each filling structure will conform to the inside surface of the aneurysm as well as to each other, thus providing a pair of tubular lumens for blood flow from the aorta to each of the iliac arteries. Preferably, the tubular lumens of each of the first and second filling structures are supported while they are being filled or after they have been filled. Still further preferably, the tubular lumens will remain supported while the filling material is hardened, thus assuring that the transitions to the tubular lumens to the native vessel lumens remain properly aligned and conformed.

In a third specific embodiment of the present invention, systems for treating aneurysms comprise at least one double-walled filling structure and at least one delivery catheter having an expandable support positionable within a tubular lumen of the filling structure. The systems will usually further comprise a suitable hardenable or curable fluid filling medium. The particular characteristics of the filling structure and delivery balloon have been described above in connection with the methods of the present invention.

In a still further specific embodiment of the present invention, a system for treating abdominal aortic aneurysms comprises a first double-walled filling structure and a second double-walled filling structure. The first and second filling structures are adapted to be filled with a hardenable filling medium while they lie adjacent to each other within the aneurysm. The systems further comprise first and second delivery catheters which can be utilized for aligning each of the first and second filling structures properly with the right and left iliacs and the infrarenal aorta as they are being deployed, filled, and hardened.

DETAILED DESCRIPTION OF THE INVENTION

Figure 1:
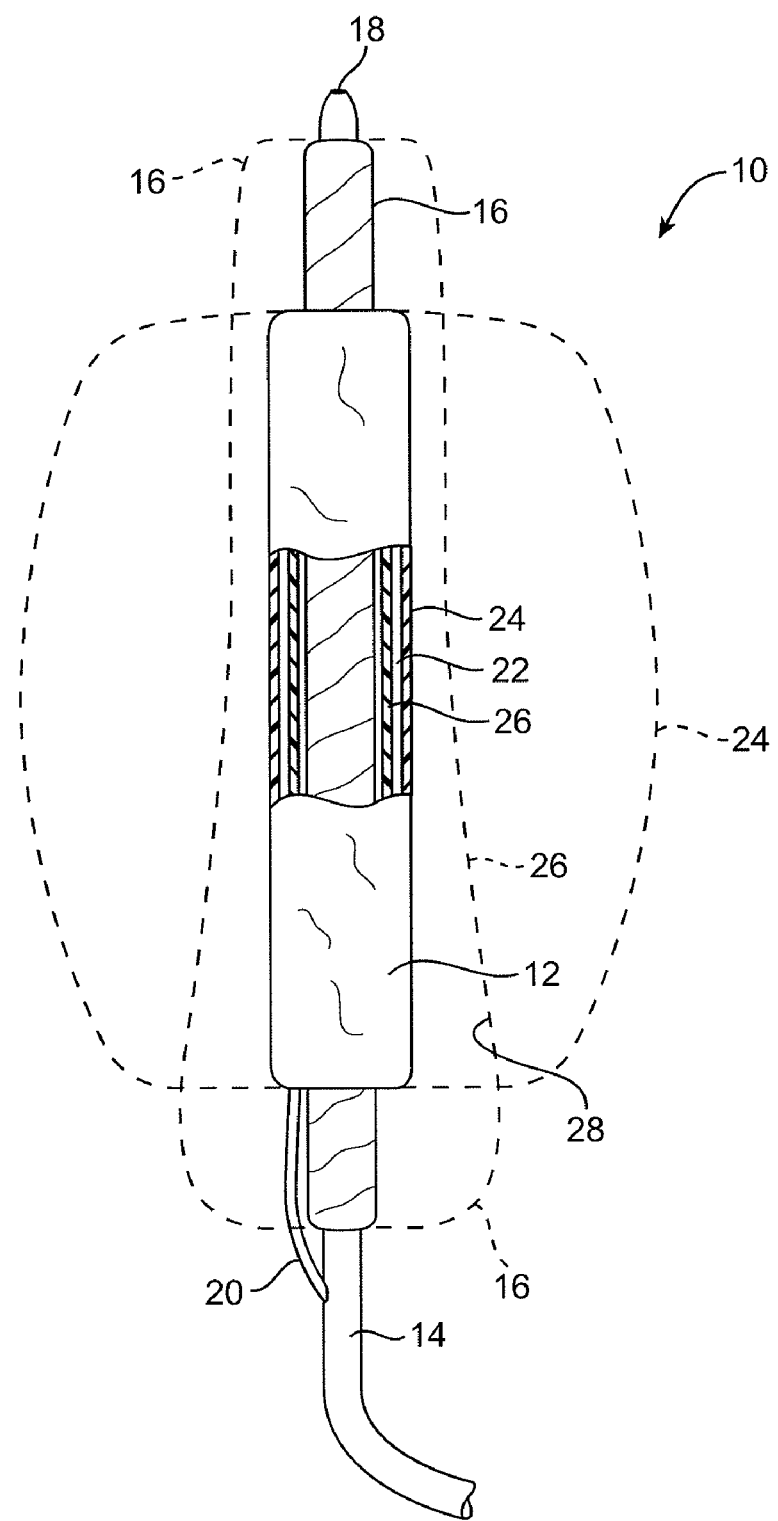
FIG. 1 illustrates a single prosthesis system comprising a filling structure mounted over a delivery catheter.

A system 10 constructed in accordance with the principles of the present invention for delivering a double-walled filling structure 12 to an aneurysm includes the filling structure and a delivery catheter 14 having an expandable element 16, typically an inflatable balloon, at its distal end. The catheter 14 will comprise a guidewire lumen 18, a balloon inflation lumen (not illustrated) or other structure for expanding other expandable components, and a filling tube 20 for delivering a filling medium or material to an internal space 22 of the double-walled filling structure 12. The internal space 22 is defined between an outer wall 24 and inner wall 26 of the filling structure. Upon inflation with the filling material or medium, the outer wall will expand radially outwardly, as shown in broken line, as will the inner wall 26, also shown in broken line. Expansion of the inner wall 26 defines an internal lumen 28. The expandable balloon or other structure 16 will be expandable to support an inner surface of the lumen 28, as also in broken line in FIG. 1.

Figure 2:
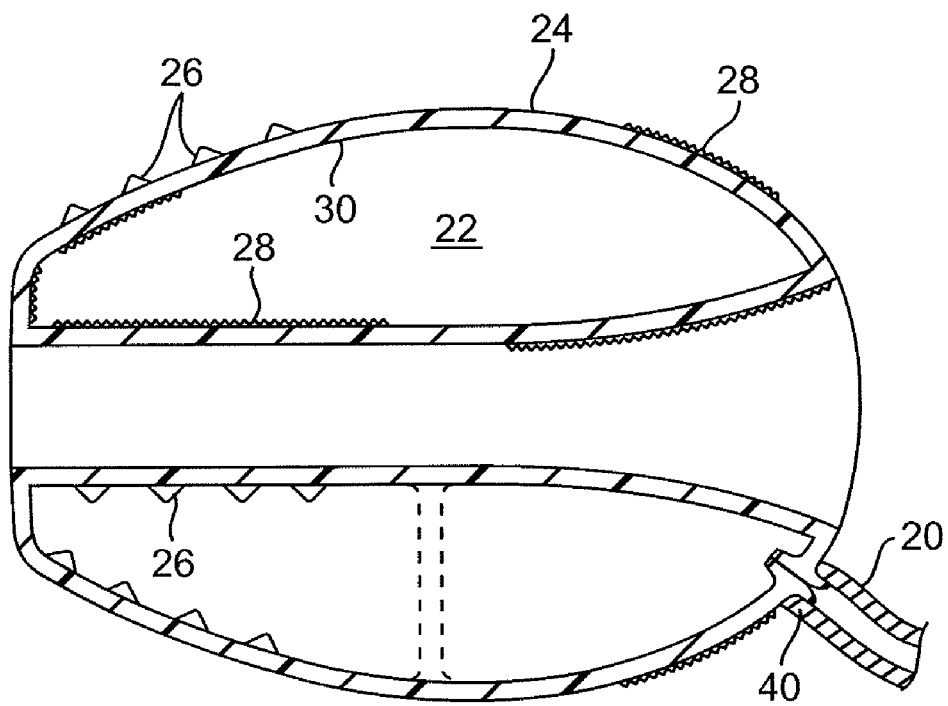
FIG. 2 is a cross-sectional view of the filling structure of FIG. 1 illustrating various surface modifications and a filling valve.

Referring now to FIG. 2, and the various internal and external surfaces may be shaped, coated, treated, or otherwise modified, to provide for a number of particular features in accordance with the principles of the present invention. For example, the outer wall 24 may be shaped to have rings, stipples, or other surface features which are typically formed into the material of the structure at the time of molding, vapor deposition, or other manufacturing process. The outer surface may also be coated with materials 28 which can be adhesives, drugs, active substances, fibers, flocking, foams, or a variety of other materials. In most cases, such surface features or modifications will be intended to enhance sealing or attachment of the outer wall 24 to the inner surface of the aneurysm being treated.

The inner surface 30 of the filling volume 22 may also be modified by providing features, coatings, surface roughening, or a variety of other modifications. The purpose of such internal features is typically to enhance adherence of the walls to the filling material or medium as the medium is cured or otherwise hardened. In some instances, materials may be coated on all or a portion of the inside surface 30 to induce or catalyze hardening of the filling material as it is being introduced.

The double-walled filling structure 12 will typically comprise at least one valve 40 to permit the introduction of the filling material or medium into the internal volume 22. As illustrated, the valve 40 may be a simple flap valve. Other more complex ball valves, and other one-way valve structures may be provided. In other instances, two-way valve structures may be provided to permit both filling and selective emptying of the internal volume 22. In other instances, the filling tube may comprise a needle or other filling structure to pass through the valve 40 to permit both filling and removal of filling medium.

Figure 3A:
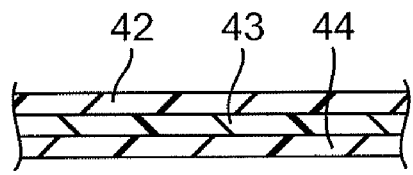
FIGS. 3A-3C illustrate alternative wall structures for the filling structure.
Figure 3B:
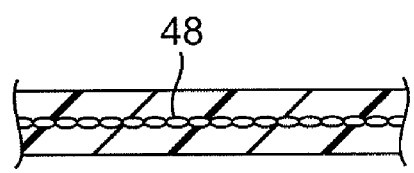
Figure 3C:
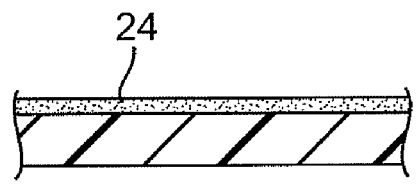

As illustrated in FIG. 2, the wall structure of the double-walled filling structure may be a single layer, typically molded or otherwise conventionally formed. The wall structures may also be more complex, as illustrated for example, FIGS. 3A-3C. FIG. 3A shows a multi-layered wall comprising layers 42, 43 and 44. It will be appreciated that such multiple layer structure can provide for increased strength, puncture resistance, variations in compliance and/or flexibility, differences in resistance to degradation, and the like. As shown in FIG. 3B, a single wall or multiple wall structure can be reinforced by braid, coils, or other metal or non-polymeric reinforcement layers or structures. As shown in FIG. 3C, the external surface 24 of the wall may be covered with drugs, fibers, protrusions, holes, active agents or other substances for a variety of purposes.

Figure 4:
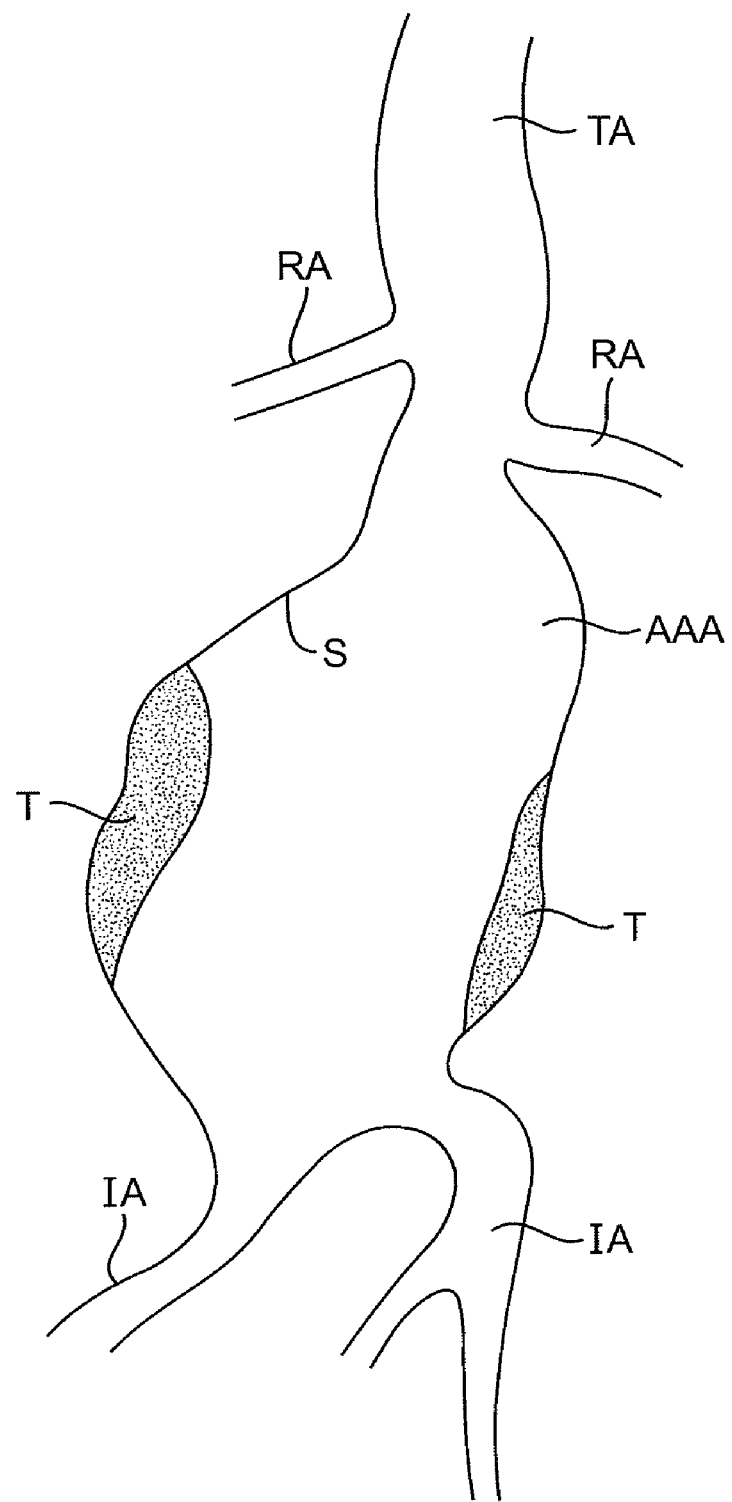
FIG. 4 illustrates the anatomy of an infrarenal abdominal aortic aneurysm.

Referring now to FIG. 4, the anatomy of an infrarenal abdominal aortic aneurysm comprises the thoracic aorta (TA) having renal arteries (RA) at its distal end above the iliac arteries (IA). The abdominal aortic aneurysm (AAA) typically forms between the renal arteries (RA) and the iliac arteries (IA) and may have regions of mural thrombus (T) over portions of its inner surface (S).

Figure 5A:
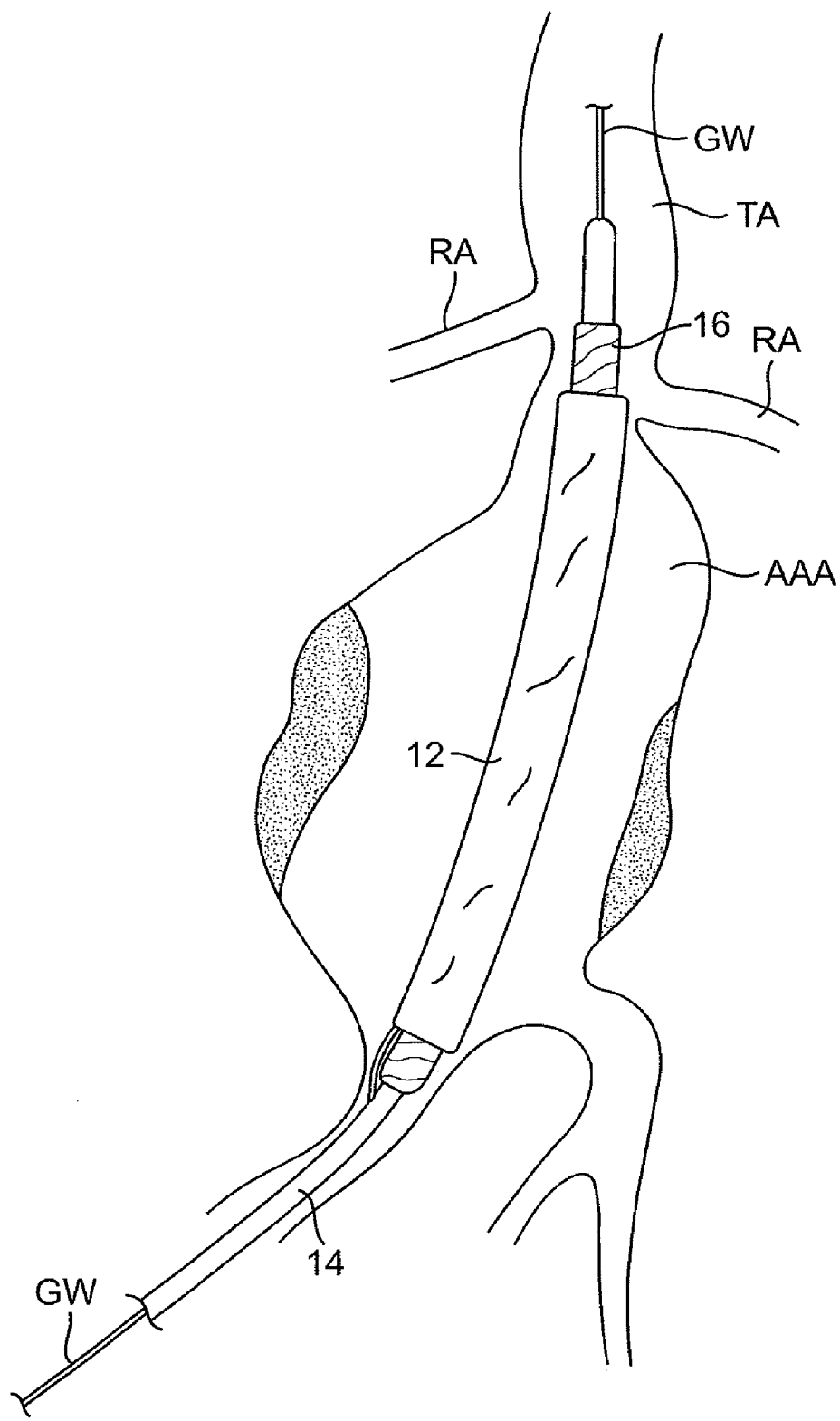
FIGS. 5A-5D illustrate use of the prosthesis system of FIG. 1 for treating the infrarenal abdominal aortic aneurysm.

Referring to FIGS. 5A-5D, the treatment system 10 of FIG. 1 may be utilized to treat the complex geometry of the transmural abdominal aortic aneurysm (AAA) of FIG. 4 by first positioning the delivery catheter 14 to place the double-walled filling structure 12 (in its unfilled configuration) generally across the aneurysm from the region of the aorta beneath the renal arteries (RA) to a region over the iliac arteries (IA), as best seen FIG. 5A. Usually, the delivery catheter 14 will be introduced over a guidewire, (GW) through a puncture in the patient's groin accessing the iliac artery by the Seldinger technique.

After the double-walled filling structure 12 is properly positioned, a hardenable inflation medium is introduced into the internal space 22 filling of the inner space 22 expands the outer wall 24 of the structure outwardly so that it conforms to the inner surface (S) of the aneurismal space.

Figure 5B:
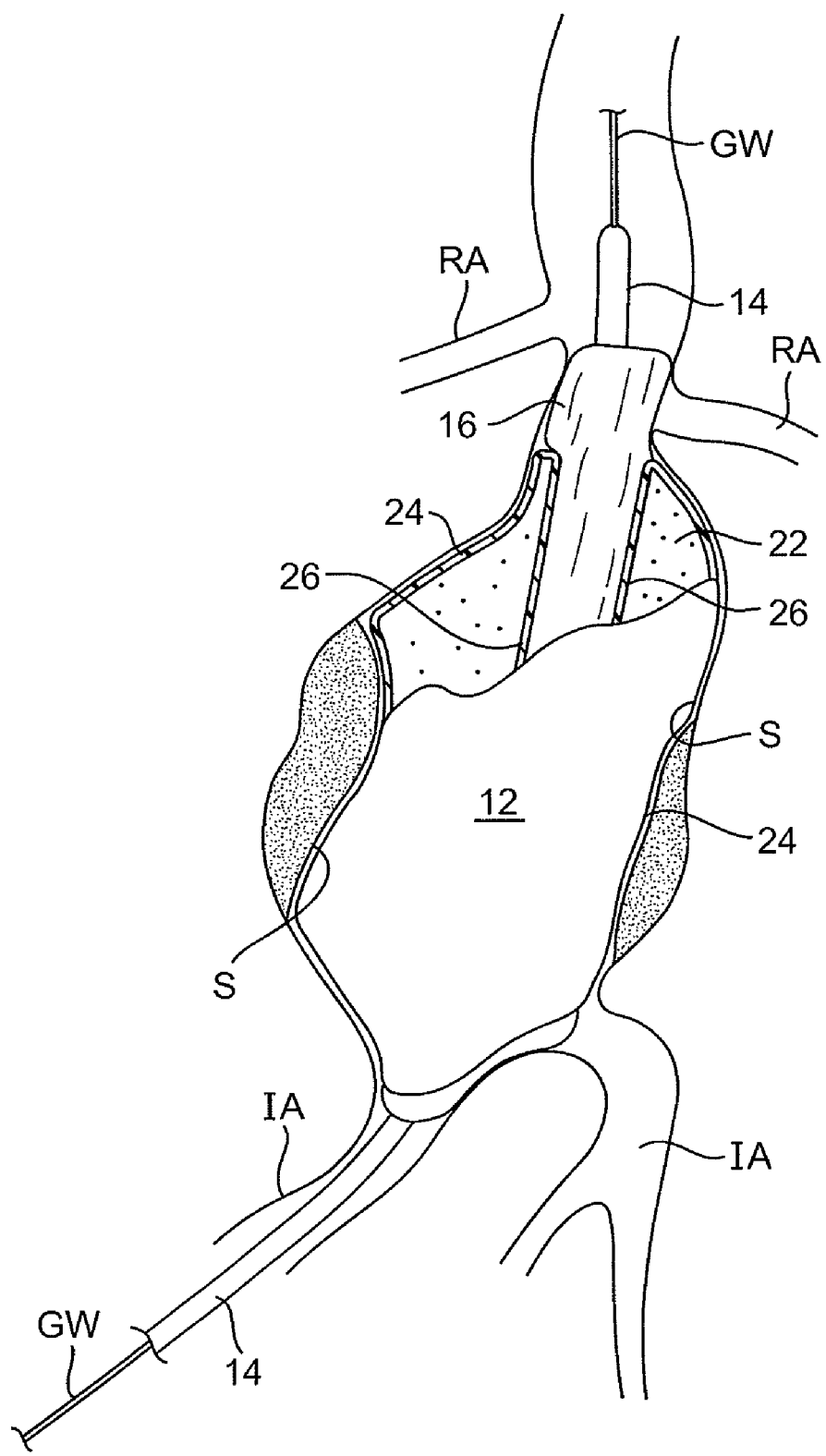
Figure 5C:
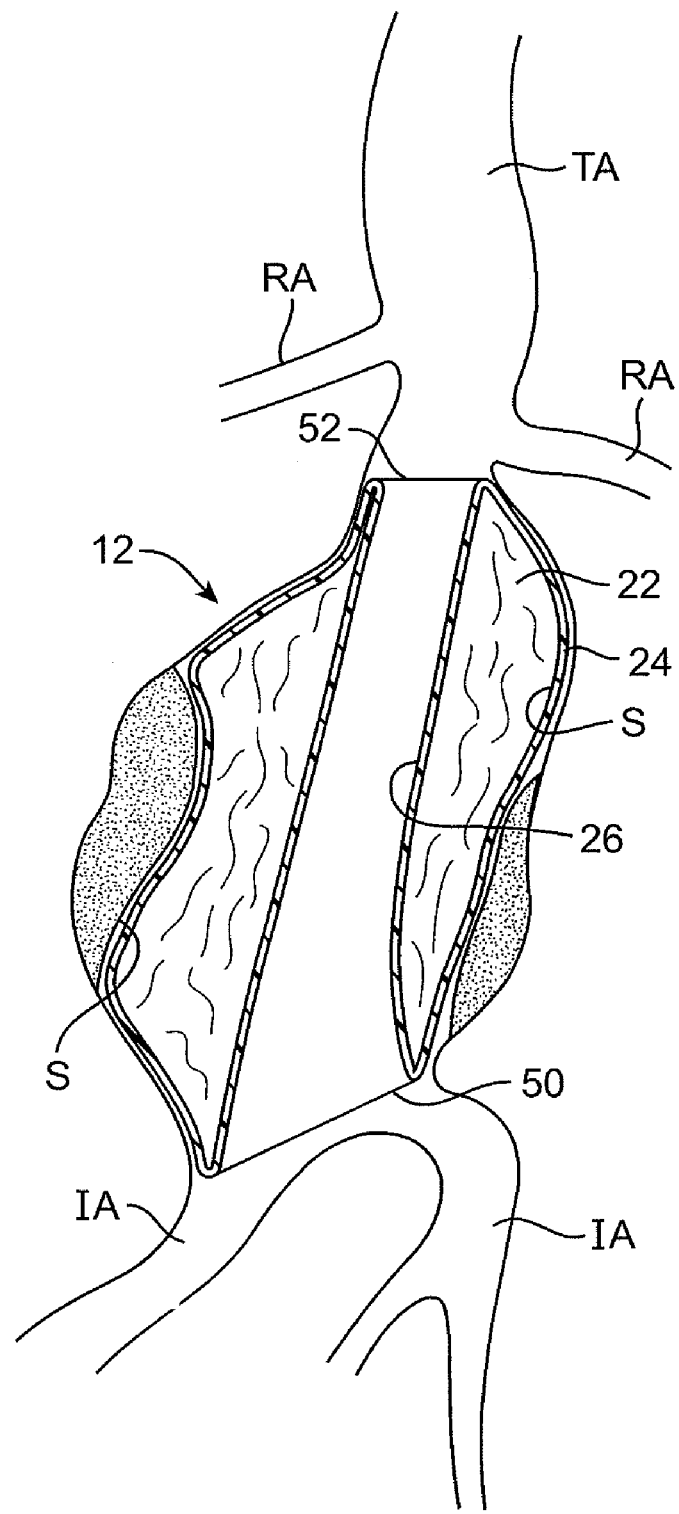

Before, during, or after filling of the double-walled filling structure 12 with inflation medium, as illustrated in FIG. 5B, the balloon 16 or other expansible structure will also be inflated or expanded to open the tubular lumen defined by the interior of the inner wall 26. In a preferred embodiment, the balloon 16 will be generally non-compliant, typically having a maximum diameter of width which is at or slightly larger than the desired tubular lumen diameter or width through the deployed filling structure 12. The filling structure 12, in contrast, will be partially or completely formed from a generally compliant material, thus allowing the non-compliant balloon or other expansible structure 16 to fully open the tubular lumen and conform the ends of the lumens to the aorta and iliac walls, as illustrated in FIG. 5C. A lower or proximal end 50 of the tubular lumen will be flared to a larger diameter so that it can accommodate the openings into both of the iliac arteries (IA) as illustrated. Thus, it will be preferred to utilize a filling structure 12 geometry which has been chosen or fabricated to match the particular patient geometry being treated. It will also be preferable to use a balloon 16 or other expansible structure which will be shaped to preferentially open the lower proximal end 50 of the tubular lumen to a larger diameter than the upper or distal end 52.

After the filling material has been introduced to the filling structure 12, typically through the filling tube 20, the fluid filling material must be cured or otherwise hardened to provide for the permanent implant having a generally fixed structure which will remain in place in the particular aneurismal geometry. Methods for curing or hardening the filling material will depend on the nature of the filling material. For example, certain polymers may be cured by the application of energy, such as heat energy or ultraviolet light. Other polymers may be cured when exposed to body temperature, oxygen, or other conditions which cause polymerization of the fluid filling material. Still others may be mixed immediately prior to use and simply cure after a fixed time, typically minutes. Often, after the filling material has been hardened, the delivery catheter 12 may be removed and the filling structure left in place as the completed prosthetic implant.

Figure 5D:
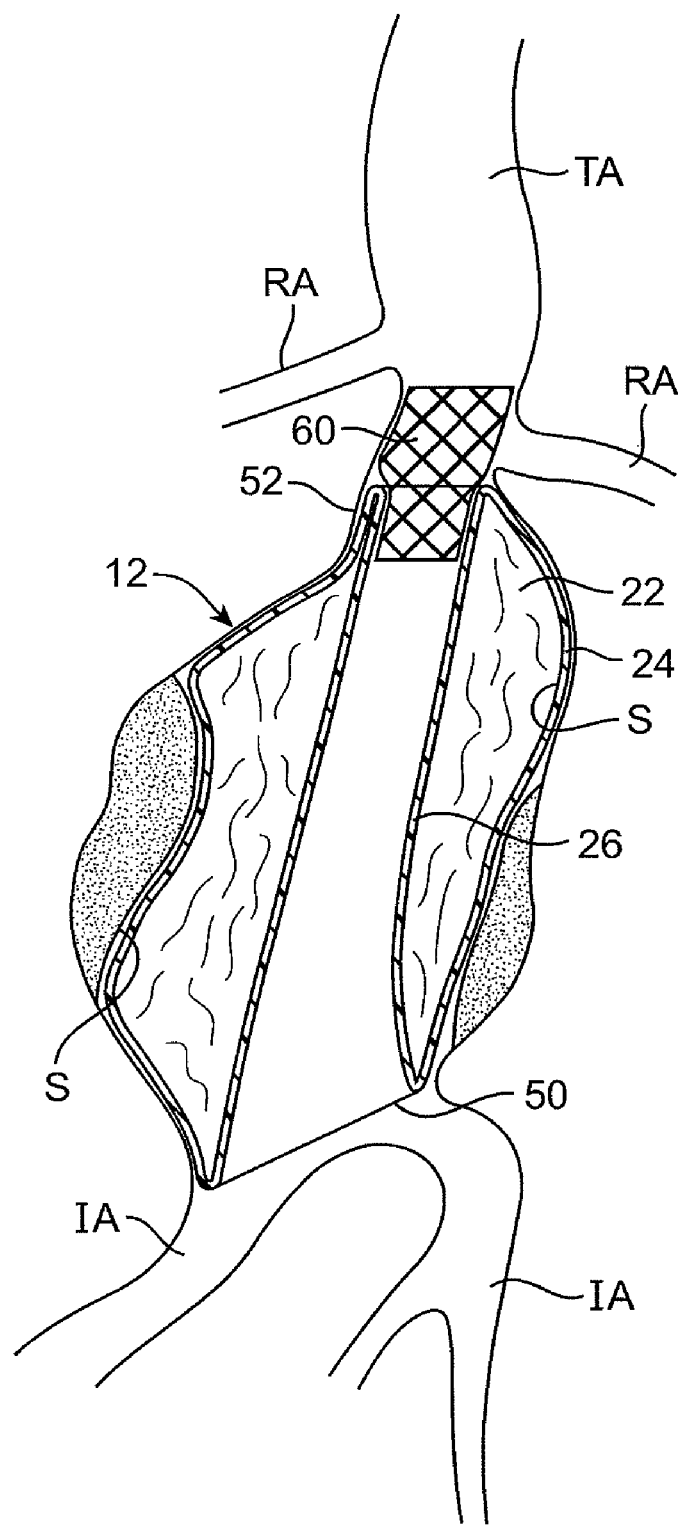

In other cases, however, it may be desirable to further position certain seals, anchors, stents, or other additional prosthetic components at either the proximal end 52 or distal end 50 of the graft. As illustrated in FIG. 5D, for example, a stent-like structure may be planted in the upper proximal opening 52 of the tubular lumen of the filling structure 12 in order to help anchor the structure, help prevent intrusion of blood into the region between the outer wall 24 and inner surface (S) of the aneurysm, and to generally improve the transition from the aorta into the tubular lumen. The sealing or anchoring structure may simply comprise a stent-like component, preferably having a port or other access route to allow blood flow into the covered renal arteries (if any). Alternatively, the anchor structure could be another inflatable unit, such as the anchor described in co-pending, commonly owned application Ser. No. 10/668,901 (published as US2004/0116997A1), the full disclosure of which is incorporated herein by reference.

Figure 6:
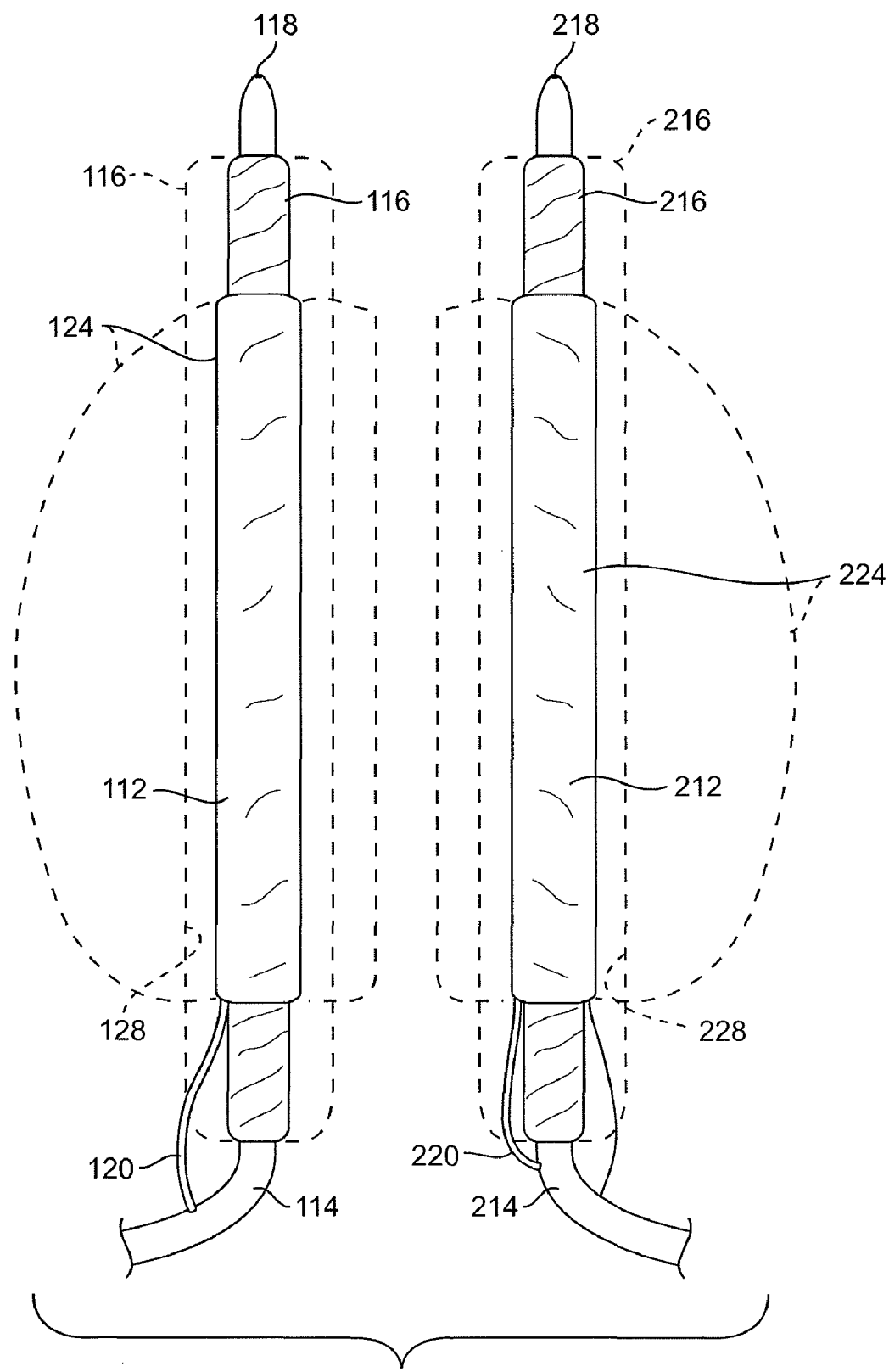
FIG. 6 illustrates a system in accordance with the principles of the present invention comprising a pair of prosthesis for delivery to an infrarenal abdominal aortic aneurysm, where each prosthesis comprises a filling structure mounted on a delivery catheter.

In a particular and preferred aspect of the present invention, a pair of double-walled filling structures will be used to treat infrarenal abdominal aortic aneurysms, instead of only a single filling structure as illustrated in FIGS. 5A-5C. A system comprising such a pair of filling structures is illustrated in FIG. 6 which includes a first filling structure 112 and a second filling structure 212. Each of the filling structures 112 and 212 are mounted on delivery catheters 114 and 214, respectively. The components of the filling structures 112 and 212 and delivery catheters 114 and 214 are generally the same as those described previously with respect to the single filling structure system 10 of FIG. 1. Corresponding parts of each of the fillings systems 112 and 212 will be given identical numbers with either the 100 base number or 200 base number. A principal difference between the filling structures 112 and 212, on the one hand, and the filling structure 12 of FIG. 1 is that the pair of filling structures will generally have asymmetric configurations which are meant to be positioned adjacent to each other within the aneurismal space and to in combination fill that space, as will be described with specific reference to FIG. 7A-7F below.

Figure 7A:
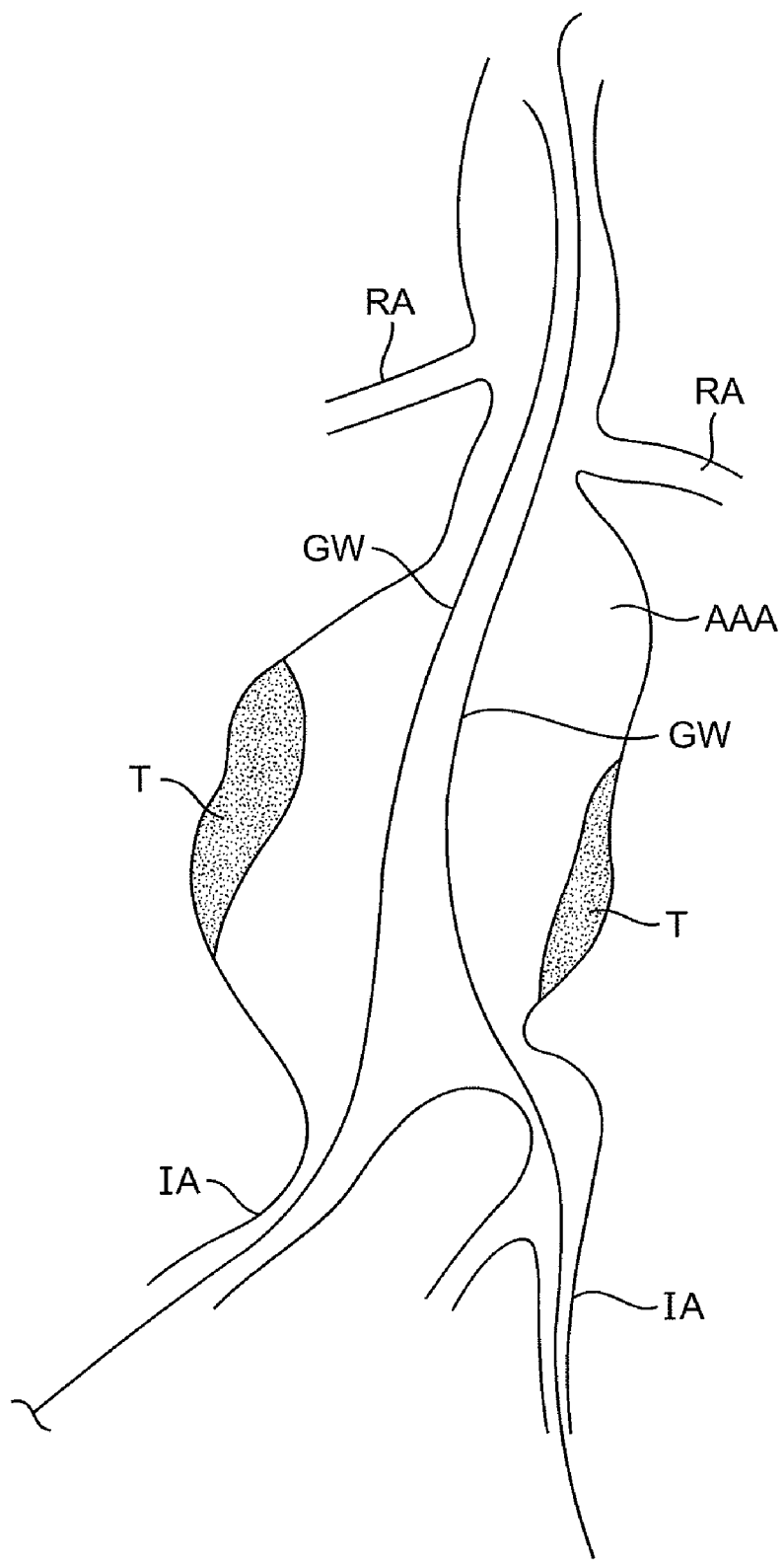
FIGS. 7A-7F illustrate use of the prosthesis system of FIG. 6 for treating an infrarenal abdominal aortic aneurysm.
Figure 7B:
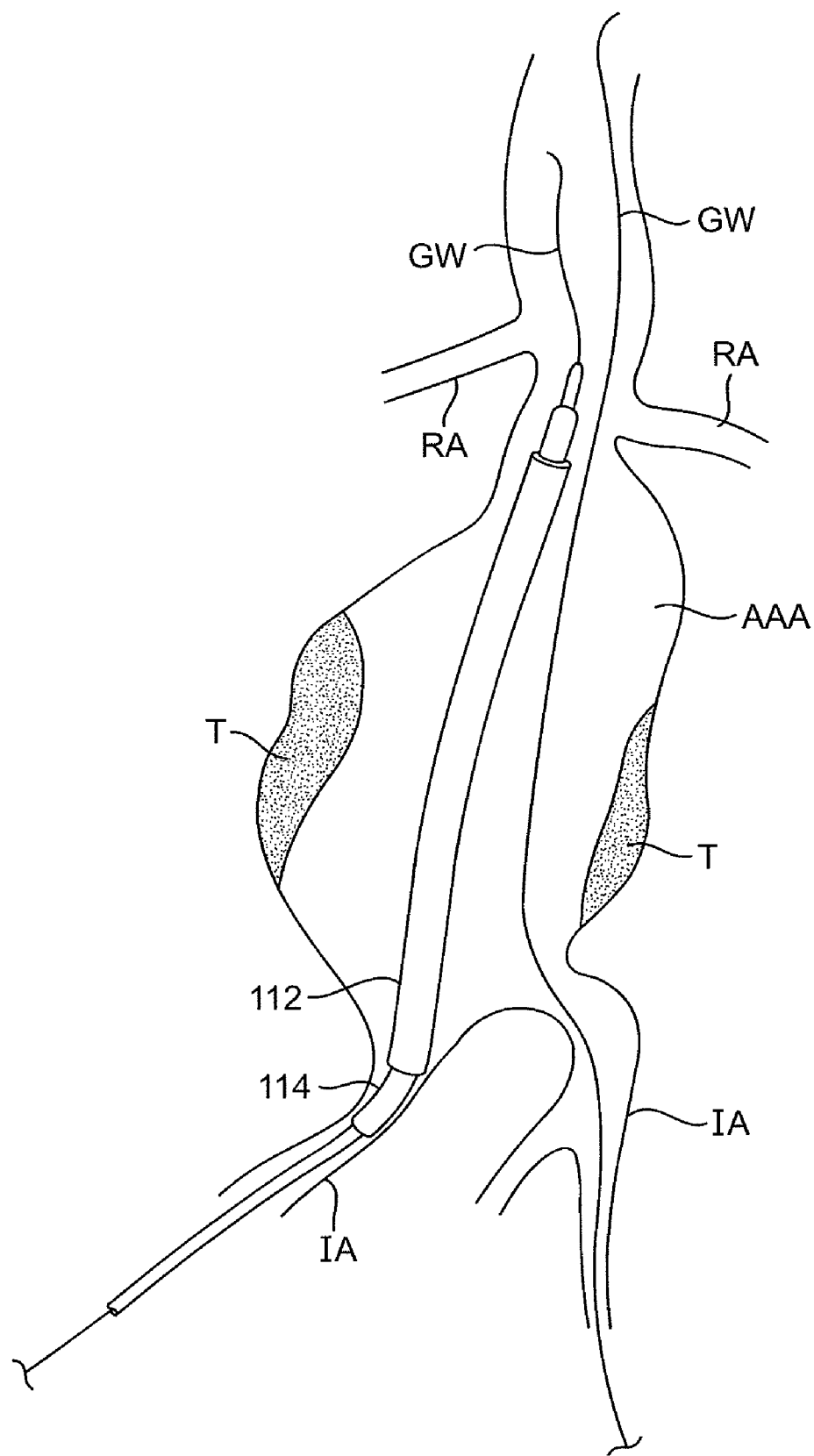
Figure 7C:
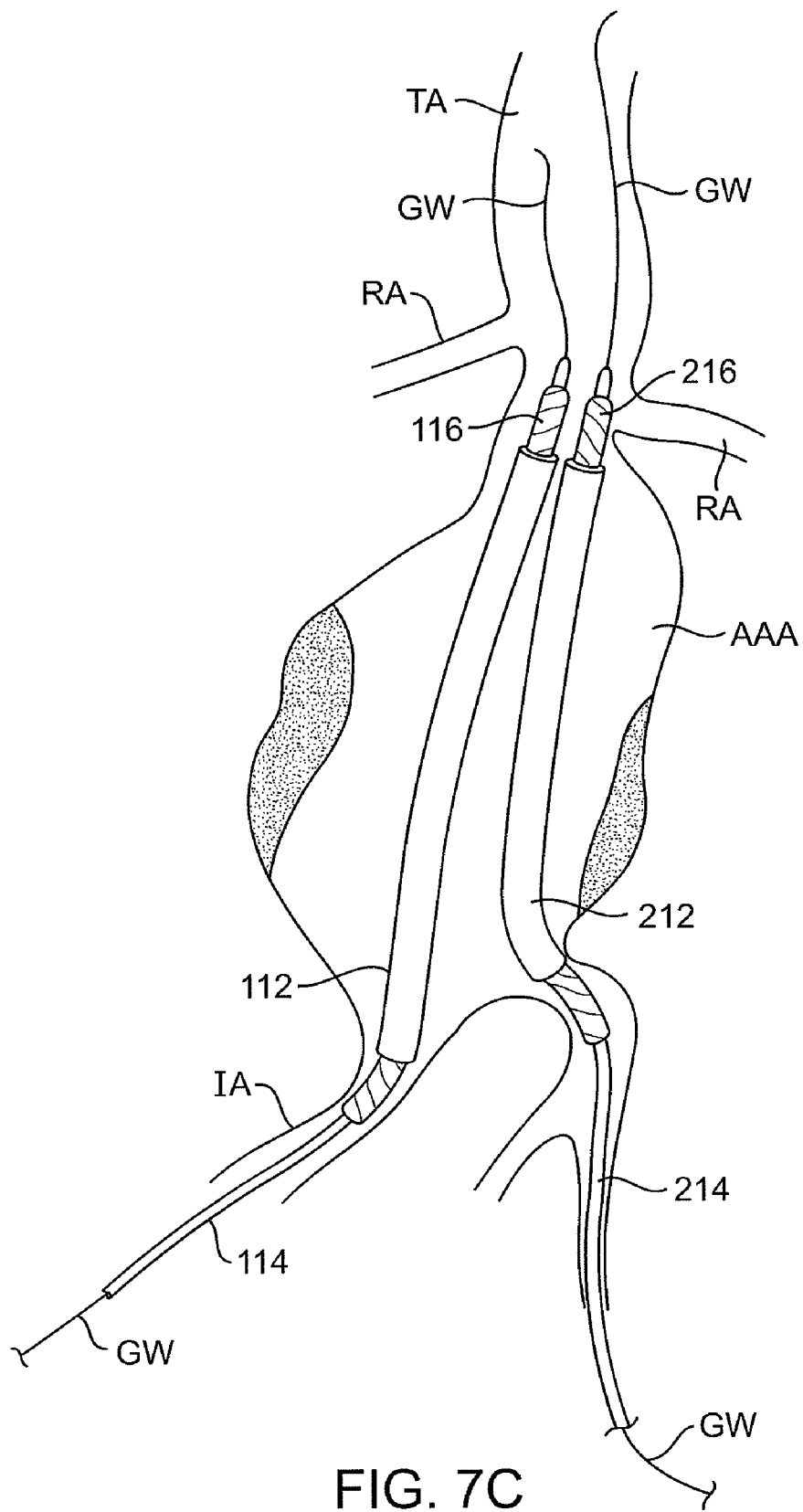
Figure 7D:
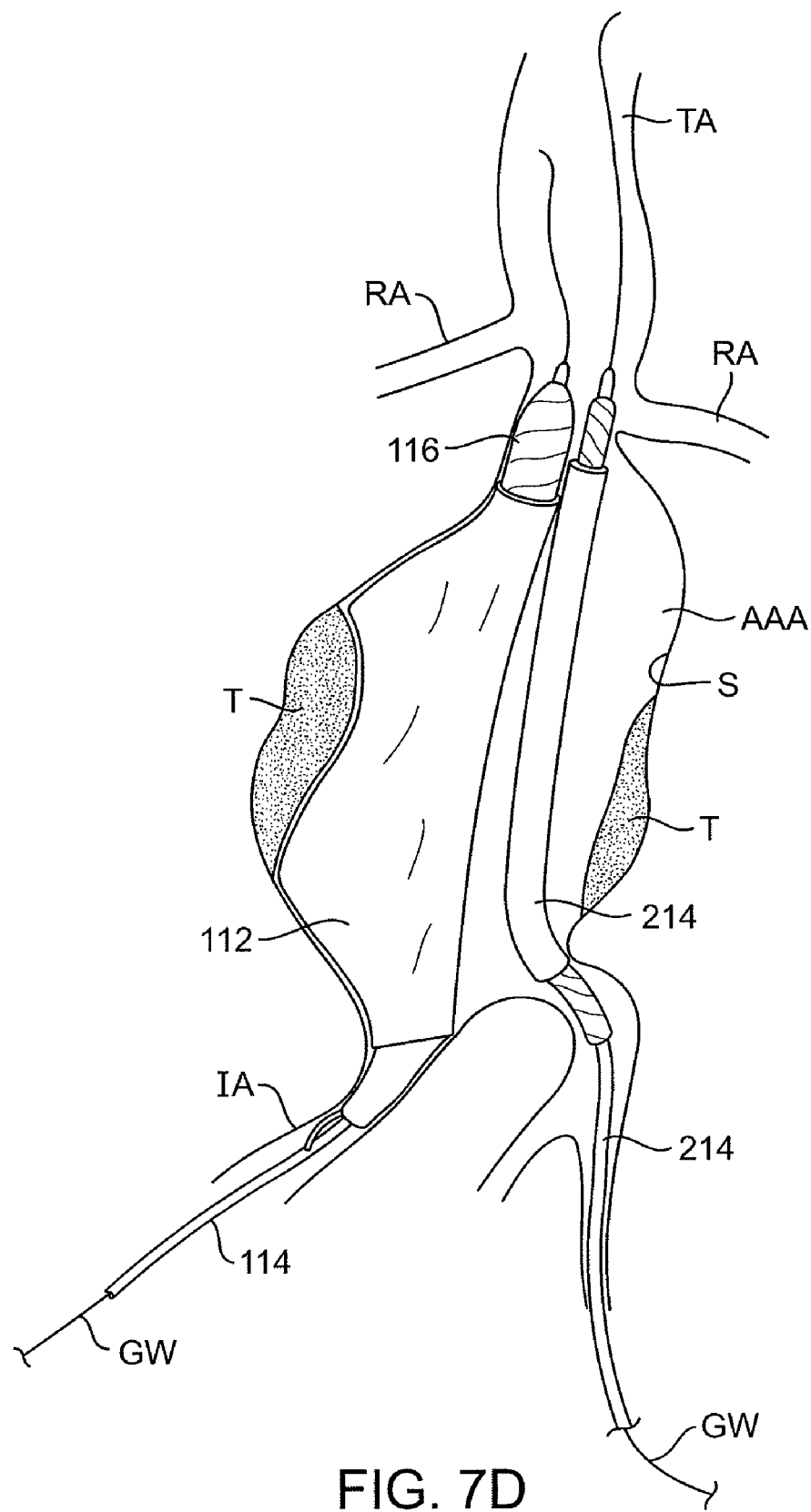
Figure 7E:
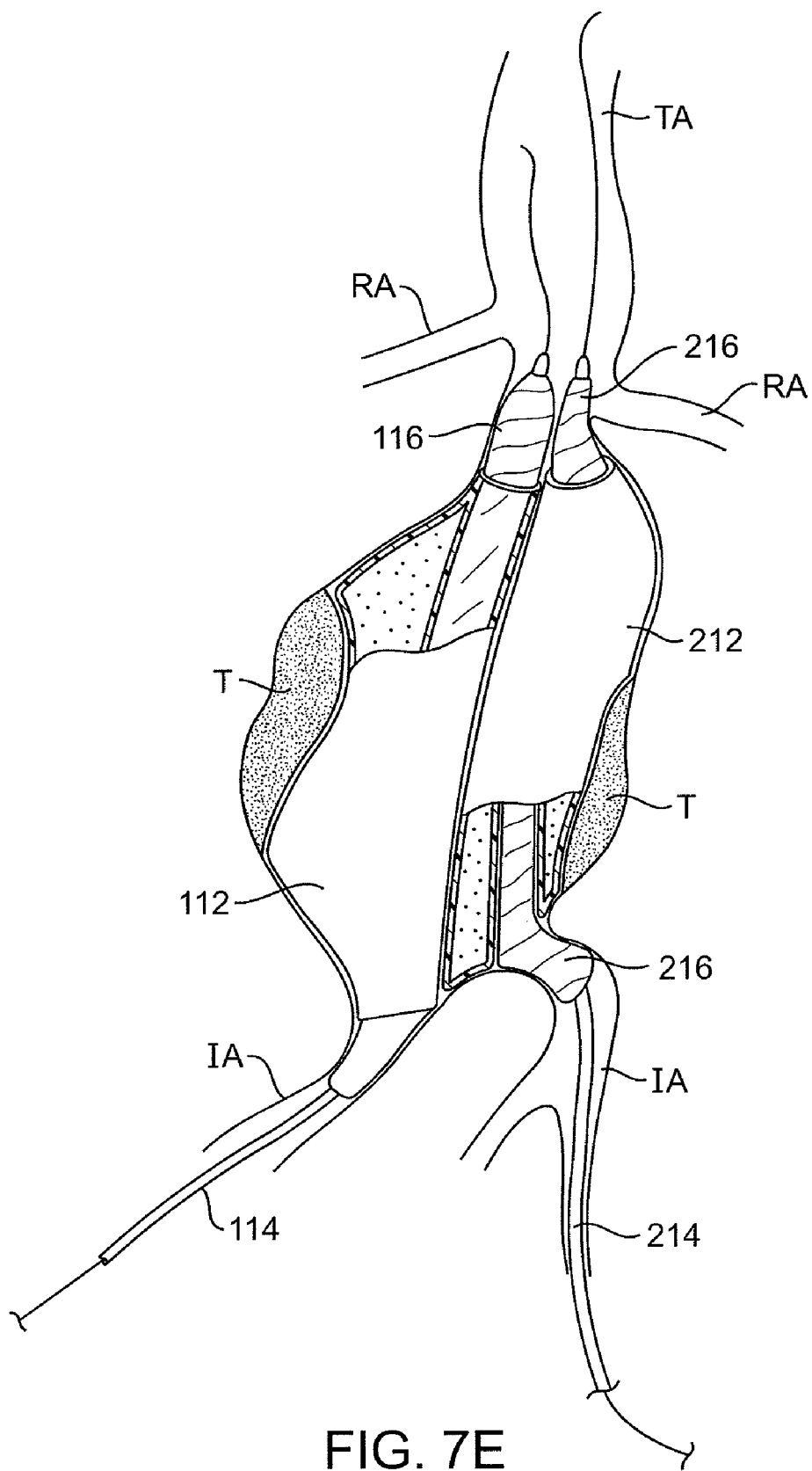

In treating an infrarenal abdominal aortic aneurysm using the pair of filling structures 112 and 212 illustrated in FIG. 6, a pair of guidewires (GW) will first be introduced, one from each of the iliac arteries (IA). As illustrated in FIG. 7A. The first delivery catheter 114 will then be positioned over one of the guidewires to position the double-walled filling structure 112 across the aortic aneurysm (AAA), as illustrated in FIG. 7B. The second delivery catheter 214 is then delivered over the other guidewire (GW) to position the second filling structure 212 adjacent to the first structure 112 within the aneurysm (AAA), as illustrated in FIG. 7C. Typically, one of the filling structures and associated balloons will be expanded first, followed by the other of the filling structures and balloon, as illustrated in FIG. 7D where the filling structure 112 and balloon 116 are inflated to fill generally half of the aneurismal volume, as illustrated in FIG. 7D. Filling can generally be carried out as described above with the one filling structure embodiment, except of course that the filling structure 112 will be expanded to occupy only about one-half of the aneurismal volume. After the first filling structure 112 has been filled, the second filling structure 212 may be filled, as illustrated in FIG. 7E. The upper ends of the balloons 116 and 216 will conform the tubular lumens of the filling structures against the walls of the aorta as well as against each other, while the lower ends of the balloons 116 and 216 will conform the tubular lumens into the respective iliac (IA).

Figure 7F:
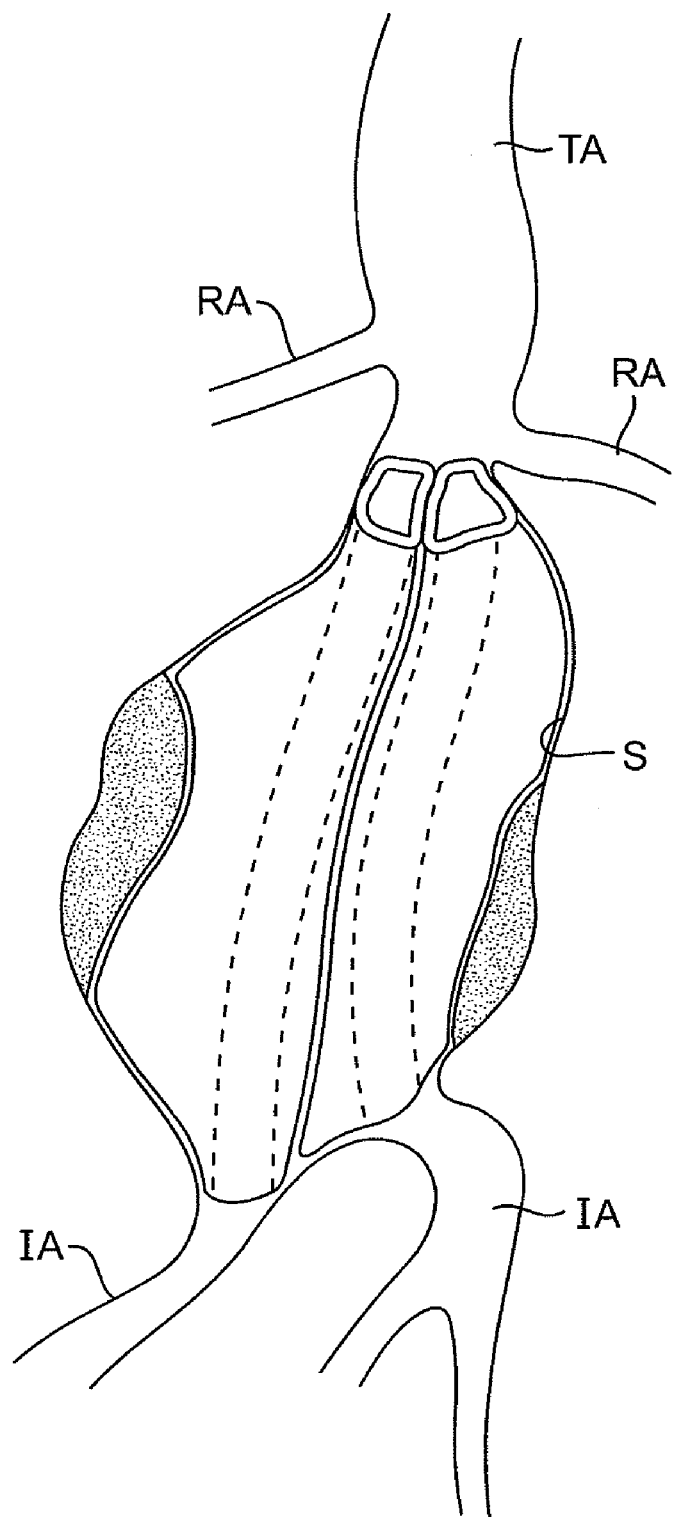

After filling the filling structures 112 and 212 as illustrated in FIG. 7E, the filling materials or medium will be cured or otherwise hardened, and the delivery catheters 114 and 214 removed, respectively. The hardened filling structures will then provide a pair of tubular lumens opening from the aorta beneath the beneath the renal arteries to the right and left iliac arteries, as shown in broken line in FIG. 7. The ability of the filling structures 112 and 212 to conform to the inner surface (S) of the aneurysm, as shown in FIG. 7F, helps assure that the structures will remain immobilized within the aneurysm with little or no migration. Immobilization of the filling structures 112 and 114 may be further enhanced by providing any of the surface features described above in connection with the embodiments of FIG. 2. Optionally, and not illustrated, anchoring or sealing structures could be provided in either of the upper or proximal openings of the tubular lumens into the aorta or from either of the distal or lower openings into the respective iliac arteries.

What is claimed is:

1. A method for treating an aneurysm, said method comprising:
   positioning a first double-walled filling structure across the aneurysm, the filling structure having an inner wall and an outer wall;
   positioning a second double-walled filling structure across the aneurysm, the filling structure having an inner wall and an outer wall, wherein the second filling structure is separate and distinct from the first filling structure and positioned adjacent the first filling structure;
   filling the first filling structure with a first fluid filling medium so that the outer wall conforms to the inside of the aneurysm;
   removing the first fluid filling medium from the first filling structure;
   filling the first filling structure with a second fluid filling medium so that the outer wall conforms to the inside of the aneurysm and the inner wall forms a first generally tubular lumen to provide for blood flow to a first iliac artery, wherein the filling structure is filled at a first filling pressure;
   filling the second filling structure with the first fluid filling medium so that the outer wall conforms to the inside of the aneurysm;
   removing the first fluid filling medium from the second filling structure;
   filling the second filling structure with the second fluid filling medium so that the outer wall conforms to the inside of the aneurysm so that, in combination, the first and second filling structure fills the aneurysmal space, and the inner wall of the second filling structure forms a second generally tubular lumen to provide for blood flow to a second iliac artery, wherein the filling structure is filled at a second filling pressure;
   expanding a first tubular support in the aneurysm to a first inflation pressure, wherein the inflation pressure is greater than the first filling pressure while the first filling structure is being filled;
   expanding a second tubular support in the aneurysm to a second inflation pressure, wherein the inflation pressure is greater than the second filling pressure while the second filling structure is being filled;
   supporting the entire inner wall of the first and second tubular lumens with the first and second expanded tubular support, respectively, while and after the first and second filling structures are being filled with the second fluid filling medium, wherein the expanded tubular supports define the shape of the respective generally tubular lumen;
   allowing hardening of the second fluid filling medium disposed in the first filling structure while the first tubular lumen remains supported;
   removing the first tubular support from the first tubular lumen after the second fluid filling medium in the first filling structure has hardened;
   allowing hardening of the second fluid filling medium disposed in the second filling structure while the second tubular lumen remains supported; and
   removing the second tubular support from the second tubular lumen after the second fluid filling medium in the second filling structure has hardened.

2. A method as in claim 1, wherein the first and second filling pressures are in the range from 100 mm Hg to 1000 mm Hg and the first and second inflation pressures are in the range from 200 mm Hg to 5000 mm Hg.

3. A method as in claim 1, wherein the first fluid filling medium comprises saline.

4. A method as in claim 1, wherein the second fluid filling medium comprises a flowable polymer which is curable in situ.

5. A method as in claim 1, further comprising monitoring the filling pressure of the first and second filling structure.

6. A method as in claim 1, further comprising monitoring the inflation pressure of the first and second tubular support.

7. A method as in claim 1, wherein at least one of the first and second tubular supports comprises an inflatable balloon.

8. A method as in claim 1, wherein at least one of the first and second tubular supports comprises a mechanical structure expandable to one or more fixed diameters.

9. A method for treating an aneurysm, said method comprising:
  positioning a first double-walled filling structure across the aneurysm, the filling structure having an inner wall and an outer wall;
  positioning a second double-walled filling structure across the aneurysm, the filling structure having an inner wall and an outer wall, wherein the second filling structure is separate and distinct from the first filling structure and positioned adjacent the first filling structure;
  filling the first filling structure with a first fluid filling medium at a first filling pressure so that the outer wall conforms to the inside of the aneurysm and the inner wall forms a first generally tubular lumen to provide for blood flow to a first iliac artery;
  removing the first fluid filling medium from the first filling structure;
  filling the first filling structure with a second fluid filling medium at a second filling pressure so that the outer wall conforms to the inside of the aneurysm and the inner wall forms the first generally tubular lumen to provide for blood flow to the first iliac artery;
  filling the second filling structure with a third fluid filling medium at a third filling pressure so that the outer wall conforms to the inside of the aneurysm and the inner wall forms a second generally tubular lumen to provide for blood flow to a second iliac artery;
  removing the third fluid filling medium from the second filling structure;
  filling the second filling structure with a fourth fluid filling medium at a fourth filling pressure so that the outer wall conforms to the inside of the aneurysm and the inner wall forms the second generally tubular lumen to provide for blood flow to the second iliac artery;
  expanding a first tubular support in the aneurysm to a first inflation pressure, wherein the inflation pressure is greater than the first and the second filling pressures while the first filling structure is being filled;
  supporting the entire inner wall of the first tubular lumen with the expanded first tubular support while and after the first filling structure is being filled with the second fluid filling medium, wherein the expanded first tubular support defines the shape of the first lumen;
  allowing hardening of the second fluid filling medium disposed in the first filling structure while the first tubular lumen remains supported by the first expanded tubular support;
  removing the first tubular support from the first tubular lumen after the second fluid filling medium in the first filling structure has hardened;
  expanding a second tubular support in the aneurysm to a second inflation pressure, wherein the inflation pressure is greater than the third and fourth filling pressures while the second filling structure is being filled;
  supporting the entire inner wall of the second tubular lumen with the expanded second tubular support while and after the second filling structure is being filled with the fourth fluid filling medium, wherein the expanded second tubular support defines the shape of the second lumen;
  allowing hardening of the fourth fluid filling medium disposed in the second filling structure while the second tubular lumen remains supported by the second expanded tubular support; and
  removing the second tubular support from the second tubular lumen after the fourth fluid filling medium in the second filling structure has hardened.

10. A method as in claim 9, wherein the filling pressures are in the range from 100 mm Hg to 1000 mm Hg and the inflation pressures are in the range from 200 mm Hg to 5000 mm Hg.

11. A method as in claim 9, wherein the step of filling the first filling structure with a first fluid filling medium comprises measuring the volume of the first fluid filling medium required to fill the first filling structure to the first pressure, and the steps of filling the first filling structure with the second fluid filling medium comprises filling the first filling structure with substantially the same volume of the second fluid filling medium.

12. A method as in claim 9, wherein the first and third fluid filling medium comprise saline.

13. A method as in claim 9, wherein the second and fourth fluid filling medium comprise a flowable polymer which is curable in situ.

14. A method as in claim 9, wherein at least one of the first and second tubular supports comprises an inflatable balloon.

15. A method as in claim 9, wherein at least one of the first and second tubular lumen supports comprises a mechanical structure expandable to one or more fixed diameters.

16. A method as in claim 9 for treating an aneurysm, said method further comprising:
  filling the first filling structure with a fifth fluid filling medium so that the outer wall conforms to the inside of the aneurysm before filling with the first fluid filling medium.

17. A method as in claim 16, said method further comprising:
  filling the second filling structure with a sixth fluid filling medium so that the outer wall conforms to the inside of the aneurysm before filling with the third fluid filling medium.

18. A method as in claim 16, wherein the at least one of the fifth and sixth fluid filling medium comprises saline.

19. A method as in claim 9 wherein each of the first and second filling structures has an asymmetric configuration such that when placed adjacent to each other, the first and second filling structures fill the aneurysmal space when filled.

20. A method as in claim 9 wherein the first and second filling structure are filled simultaneously.

21. A method as in claim 9 wherein the first and second filling structures are filled sequentially.

* * * * *